(12) United States Patent
Witteler et al.

(10) Patent No.: US 6,380,338 B1
(45) Date of Patent: Apr. 30, 2002

(54) POLYMERS FOR COSMETIC FORMULATIONS

(75) Inventors: Helmut Witteler, Beindersheim; Reinhold Dieing, Schifferstadt; Axel Sanner, Frankenthal; Jacqueline Engesser, Ludwigshafen; Wilma M. Dausch, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/432,281

(22) Filed: Nov. 2, 1999

(30) Foreign Application Priority Data

Nov. 2, 1998 (DE) .......................................... 198 50 363

(51) Int. Cl.⁷ ........................... C08F 26/06; C08F 26/10
(52) U.S. Cl. ........................... 526/258; 424/47; 424/70; 424/71; 424/78.03; 424/401; 524/81
(58) Field of Search ............................. 424/47, 76, 71, 424/78.03, 401; 526/258; 524/81

(56) References Cited

U.S. PATENT DOCUMENTS

| 5,071,902 A | 12/1991 | Langerbeins et al. ........ 524/458 |
| 5,139,882 A | 8/1992 | Elser et al. .................. 428/522 |
| 5,158,762 A | 10/1992 | Pierce ........................ 424/47 |
| 5,288,602 A | 2/1994 | Geiger et al. ................ 430/539 |
| 5,536,740 A | * 7/1996 | Granger et al. ............. 514/392 |
| 5,972,431 A | * 10/1999 | Marsella et al. ............ 427/384 |

FOREIGN PATENT DOCUMENTS

| DE | 3902067 | 7/1990 |
| DE | 3902555 | 8/1990 |
| DE | 4428003 | 2/1996 |
| EP | 124713 | 11/1984 |
| WO | 97/45468 | 12/1997 |

OTHER PUBLICATIONS

Hoffbauer et al., *Aerosol and Spray Report*, 36(10), Sep. 15, 1997.
Dallal et al., *Hair and Hair Care*, 1977, p.105–165.

* cited by examiner

Primary Examiner—David W. Wu
Assistant Examiner—Tanya Zalukaeva
(74) Attorney, Agent, or Firm—Keil & Weinkauf

(57) ABSTRACT

The invention relates to cosmetic formulation comprising polymers to which groups of the formula I are bonded

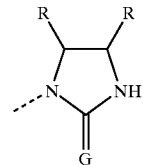

where R is H or identical or different organic radicals, which may also be bonded to one another, and G is O or NH, as hair-setting polymers.

19 Claims, 1 Drawing Sheet

POLYMERS FOR COSMETIC FORMULATIONS

Figure 1:
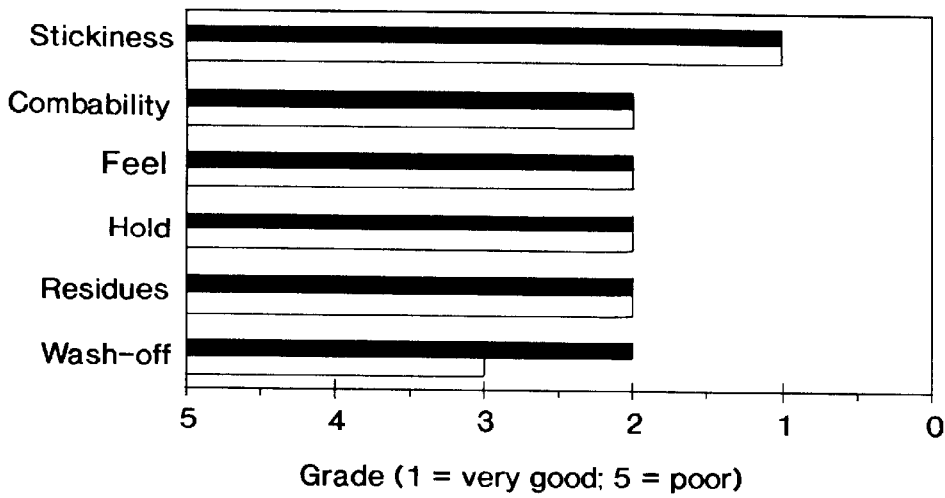

The invention relates to the use of polymers to which groups of the formula I are bonded,

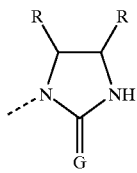

where
R is H or identical or different organic radicals, which may also be bonded to one another, and
G is O or NH,
in cosmetics and as hair-setting polymers.

Frequently, polymers are used in hair cosmetic formulations. Requirements which are placed on hair cosmetic compositions are described, inter alia, in B. Hoffbauer, R. Brott, Aerosol and Spray Report 36 (10), 9–15 (1997) and in Dale H. Johnson (editor), "Hair and Hair Care", Marcel Dekker Inc., New York 1997, p. 105–165.

Because of the continually increasing requirement for more environmentally friendly products, the content of volatile organic compounds (VOC) in cosmetic preparations, such as hairsprays, hair gels or setting foams, should be kept as low as possible or be reduced. However, the use of conventional polymers presents difficulties since, as the water content of hairspray formulations rises, their viscosity increases, and it is no longer possible to ensure uniform application of the polymer on the hair. Subsequent filming leads to unsatisfactory results in terms of shine, feel and adhesion. Attempts have been made to solve this problem by using polymers based on polyamides (DE 44 28 003) or polyesters and polyester amides (U.S. Pat. No. 5,158, 762). However, these polymers have disadvantages as regards wash-off with water or have insufficient solubility in standard commercial propellant/solvent mixtures.

DE 39 02 067 describes the use of aqueous polymer dispersions which comprise polymers in which a ureido methacrylate is also used as monomer unit for the impregnation of polyester fabrics. The advantage which is given is the reduction in formaldehyde liberatiion. The use of ureido methacrylate as copolymer improves the adhesion of the polymer to the fiber.

DE 39 02 555 describes the use of aqueous plastic dispersions which consist of polymers in which a ureido methacrylate is also used as monomer unit, for coating plastic surfaces. The advantage given is the improved adhesion on surfaces of hard PVC, polycarbonate, ABS, polystyrene and PPO.

AU 8425444 describes ureido methacrylate-containing vinyl acetate copolymers which can be used as binders for nonwoven textile fabrics. The use of ureido methacrylate as copolymer improves the adhesion of the polymer to the fiber.

WO 97/45468 reports on acetacetoxy-modified polymers having a surfactant action. These are particularly suitable as coating materials. Their use in shampoos is also mentioned. Said polymers can, in addition to acetacetoxy groups, also contain inter alia ureido methacrylate.

It is an object of the present invention to vary the composition of polymers which are customarily used, or in principle could be used, in hair cosmetic applications in such a way that their processing or application properties and their use properties improve at the same time, without certain properties such as surface activity inevitably arising. This should be the case in particular as regards setting, wash-off and viscosity during and after application. Other properties which are to be optimized become evident from the particular application. For example, for use in hairsprays, the following properties are of specific interest: viscosity, film formation, setting action, freedom from stickiness (even at high atmospheric humidity), ability to be combed out, wash-off, feel, shine, adhesion, antistatic action and solubility in water, alcohol, dimethyl ether, propane and butane and in mixtures thereof. These properties of hair-setting polymers and the characterization of polymers with regard to these properties are known to the person skilled in the art. In addition, the manufacturing costs and the activity per amount of polymer used are important.

FIG. 1 depicts the results of a comparison between the polymer of Example 1, according to the present invention, and a standard commercial polymer (Luvimer™ 100 P from BASF Aktiengesellschaft) for suitability as hair treatments. The comparison is described in Example 6 herein, The graph of FIG. 1 indicates the properties of stickiness, combability, feel, hold, residues and wash-off characteristics as assessed sensorily, and demonstrates a superior profile of these properties in the polymer of Example 1 over the commercial product Luvimer™ 100 P.

Figure 2:
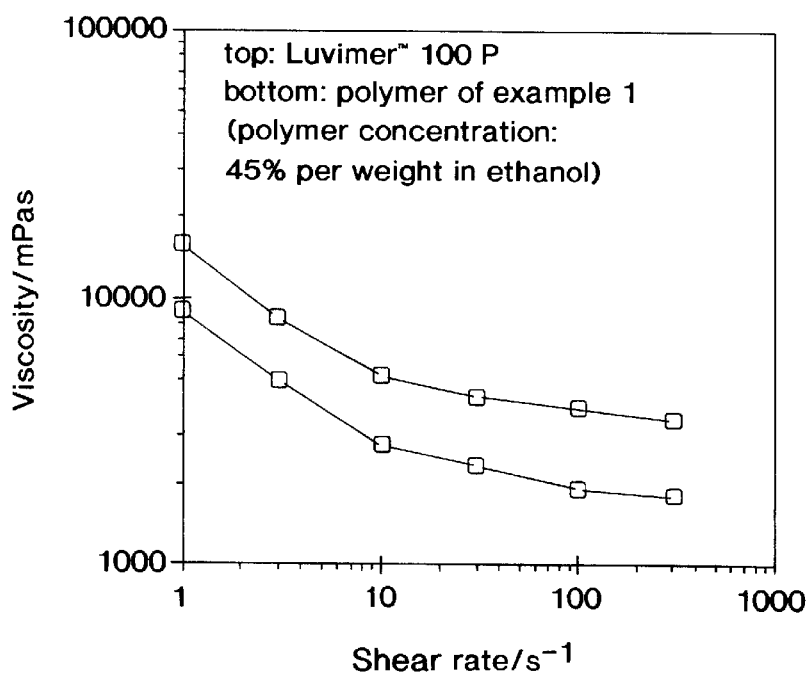

FIG. 2 depicts results of a viscosity comparison between the polymer of Example 1 and Luvimer™ 100 P. The graph indicates that the viscosity of the polymer of Example 1 is lower than that of Luvimer™ 100 P.

We have found that this object is achieved by the use of polymers to which groups of the formula I are bonded,

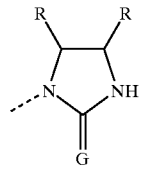

where
R is H or identical or different organic radicals, which can also be bonded to one another, and
G is O or NH,
as hair-setting polymers.

We have found that the use of the polymers P which contain a group I (derivatives of ethyleneurea) in hair cosmetic formulations is advantageous. The advantage of the novel use of the polymers P in hair cosmetic formulations is particularly evident from improved wash-off at reduced solution viscosity and unchanged setting action.

Particularly suitable polymers P for the novel use are those which are prepared using monomers of the formula II or which contain repeat units of the formula III,

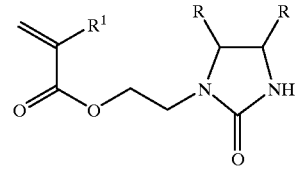

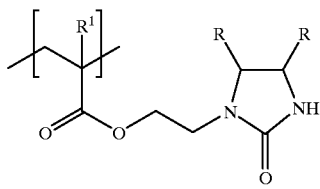

III

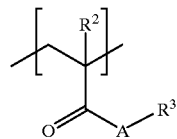

IV

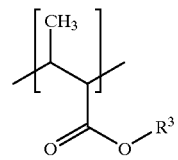

V

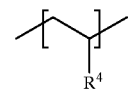

VI

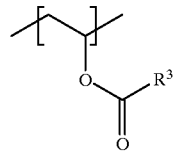

VII

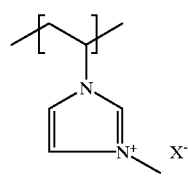

VIII where
$R^1$ is H or $CH_3$, and
R is R or H or any organic radicals, which may be identical or different and may also be bonded to one another, preferably H, or both R are the group —NH—C(O)—NH—.

Surprisingly, it has been found that the polymers P can easily be washed out of human hair, although monomers of the formula II are normally used in polymer synthesis as agents for increasing the adhesion of the polymer. While ureido methacrylate-containing binders for textiles, such as those corresponding to the prior art, give coatings whose wash-off is reduced as a result of ureido methacrylate, the polymers P for the novel intended use, for example the use as hairspray, are notable for good wash-off. In addition, when used in hairsprays, the setting action, feel and combability are equally as good as for standard commercial polymers, for example Luvimer™ 100 P from BASF Aktiengesellschaft. Other use properties being identical or better, the solution viscosity is also lower than that of Luvimer™ 100 P. This is advantageous for application as spray or aerosol. Overall, the profile of use and application properties is superior to that for commercially available products.

The polymers P can be spread out as a solution to give films. After drying, these films display greater hardnesses than standard commercial hair setting polymers. This is likewise indicative of their superior suitability for use as hair-setting compositions compared with commercial products.

The polymers P can also be used according to the invention in cosmetics. In the case of the novel use in cosmetics, for example, the advantage of the low viscosity also comes to the fore.

The polymers P can be prepared alone from monomers of the formula II or as a mixture with ethylenically unsaturated compounds. Preferably, from 0.05 to 100% by weight of the monomers used are monomers of the formula II, and from 0 to 99.95% by weight are other copolymerizable monomers.

Alternatively, it is possible to obtain the polymers P from prepolymers. Thus, for example, prepolymers, which have been prepared from acrylic acid, methacrylic acid and the esters, amides, halides and other derivatives of these acids, can be reacted to give polymers which contain a group of the formula I. In particular, using 2 hydroxyethyl (ethyleneurea) (CAS No. 3699-54-5), polymers can be obtained which contain repeat units of the type III. The polymers P synthesized in this way from prepolymers can likewise be used according to the invention for use in cosmetic and hair cosmetic preparations.

In preferred embodiments of the invention, polymers P are used for the novel intended use which are obtained by copolymerization from monomers of the formula II with suitable copolymerizable monomers (E) such that the polymers additionally contain repeat units, e.g. of the formulae IV, V, VI, VII and/or VIII, where
$R^2$ is H or methyl,
$R^3$ is H or branched or unbranched alkyl radicals or hydroxyalkyl radicals,
$R^4$ is

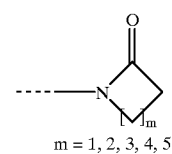

m = 1, 2, 3, 4, 5

A is O or NH,
X– is an anion, in particular Cl—, $SO_4CH_3$—, $SO_4C_2H_5$—, $H_2PO_4$—.

A particularly preferred monomer of the formula II is ureido methacrylate ($R^1=CH_3$, R=H).

Suitable copolymerizable monomers (E) which can be used are, preferably, ethylenically unsaturated monomers. Here, it is possible to use either a single monomer or combinations of two or more monomers. [lacuna].

For example, this can be solution polymerization, emulsion polymerization, reverse emulsion polymerization, suspension polymerization, reverse suspension polymerization or precipitation polymerization, without limiting the methods which can be used thereto. For solution polymerization, water or customary organic solvents can be used as solvent. Preparation in the melt is also possible.

Monomers which can be polymerized with a reaction initiated by free radicals are preferred. The term "ethylenically unsaturated" means that the monomers have at least one polymerizable carbon-carbon double bond which can be mono-, di-, tri-, or tetrasubstituted.

The monomers (E) can make up to 99.95% by weight, preferably from 85 to 98% by weight, of the polymer P.

The preferred ethylenically unsaturated monomers (E) can be described by the following general formula:

X—C(O)CR$^7$=CHR$^6$ where

X is chosen from the group os radicals —OH, —OM, —OR$^8$, NH$_2$, —NHR$^8$, N(R$^8$)$_2$;

M is a cation chosen from the group consisting of Na+, K+, Mg++, Ca++, Zn++, NH$_4$+, alkylammonium, dialkylammonium, trialkylammonium and tetraalkylammonium;

the radicals R$^8$ can be identical or different and are chosen from the group consisting of —H, $C_1$–$C_{40}$ linear or branched-chain alkyl radicals, N,N-dimethylaminoethyl, 2-hydroxyethyl, 2-methoxyethyl, 2-ethoxyethyl, hydroxypropyl, methoxypropyl or ethoxypropyl.

R$^7$ and R$^6$ are, independently of one another, chosen from the group consisting of —H, $C_1$–$C_8$ linear or branched-chain alkyl chains, methoxy, ethoxy, 2-hydroxyethoxy, 2-methoxyethoxy and 2-ethoxyethyl.

Representative but nonlimiting examples of suitable monomers (E) are, for example, acrylic acid and the salts, esters and amides thereof. The salts can be derived from any desired nontoxic metal, ammonium or substituted ammonium counterions.

The esters can be derived from $C_1$–$C_{40}$ linear, $C_3$–$C_{40}$ branched-chain, or $C_3$–$C_{40}$ carbocyclic alcohols, from polyfunctional alcohols having from 2 to about 8 hydroxyl groups, such as ethylene glycol, hexene glycol, glycerol, and 1,2,6-hexanetriol, from aminoalcohols or from alcohol ethers, such as methoxyethanol and ethoxyethanol, or polyethylene glycols.

Also suitable are N,N-dialkylaminoalkyl acrylates and methacrylates and N-dialkylaminoalkylacryl- and methacrylamides of the formula (EII)

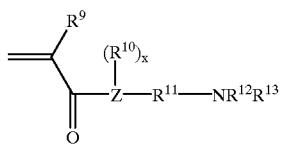

(EII)

where

R$^9$=H, alkyl having from 1 to 8 carbon atoms,

R$^{10}$=H, methyl,

R$^{11}$=alkylene having from 1 to 24 carbon atoms, optionally substituted by $C_1$–$C_6$-alkyl, R$^{12}$, R$^{13}$=$C_1$–$C_{40}$ alkyl radical, Z=nitrogen where x=1, or oxygen where x=0.

The amides can be unsubstituted, N-alkyl- or N-alkylamino-monosubstituted or N,N-dialkyl-substituted or N,N-dialkylamino disubstituted, the alkyl or alkylamino groups being derived from $C_1$–$C_{40}$ linear, $C_3$–$C_{40}$ branched-chain, or $C_3$–$C_{40}$ carbocyclic units. In addition, the alkylamino groups can be quaternized.

Preferred monomers of the formula EII are N,N-dimethylaminomethyl (meth)acrylate, N,N-diethylaminomethyl (meth)acrylate, N,N-dimethylaminoethyl (meth)acrylate, N,N-diethylaminoethyl (meth)acrylate.

Other monomers (E) which can be used are substituted acrylic acids and salts, esters and amides thereof, the substituents being on the carbon atoms in the two or three position of the acrylic acid, and being chosen independently of one another from the group consisting of $C_1$–$C_4$ alkyl, CN, COOH, particularly preferably methacrylic acid, ethacrylic acid and 3-cyanoacrylic acid. These salts, esters and amides of these substituted acrylic acids can be chosen as described above for the salts, esters and amides of acrylic acid.

Other suitable monomers (E) are vinyl and allyl esters of $C_1$–$C_{40}$ linear, $C_3$–$C_{40}$ branched-chain or $C_3$–$C_{40}$ carbocyclic carboxylic acids (e.g. vinyl acetate, vinyl propionate, vinyl neononanoate, vinyl neoundecanoic acid or vinyl t-butylbenzoate); vinyl or allyl halides, preferably vinyl chloride and allyl chloride, vinyl ether, preferably methyl, ethyl, butyl, or dodecyl vinyl ether, vinylformamide, vinylmethylacetamide, vinylamine; vinyllactams, preferably vinylpyrrolidone and vinylcaprolactam, vinyl- or allyl-substituted heterocyclic compounds, preferably vinylpyridine, vinyloxazoline and allylpyridine.

Also suitable are N-vinylimidazoles of the formula EIII, in which R$^{14}$ to R$^{16}$ independently of one another are hydrogen, $C_1$–$C_4$-alkyl or phenyl:

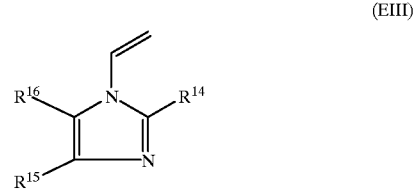

(EIII)

Other suitable monomers (E) are diallylamines of the formula (EIV)

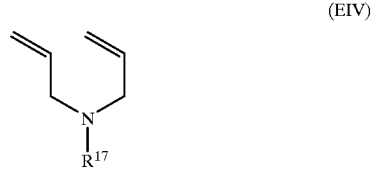

(EIV)

where R$^{17}$=$C_1$- to $C_{24}$-alkyl.

Other suitable monomers (E) are vinylidene chloride; and hydrocarbons having at least one carbon-carbon double bond, preferably styrene, alpha-methylstyrene, tert-butylstyrene, butadiene, isoprene, cyclohexadiene, ethylene, propylene, 1-butene, 2-butene, isobutylene, vinyltoluene, and mixtures of these monomers.

Particularly suitable monomers (E) are acrylic acid, methacrylic acid, ethylacrylic acid, methyl acrylate, ethyl acrylate, propyl acrylate, n-butyl acrylate, isobutyl acrylate, t-butyl acrylate, 2-ethylhexyl acrylate, decyl acrylate, methyl methacrylate, ethyl methacrylate, propyl methacrylate, n-butyl methacrylate, isobutyl methacrylate, t-butyl methacrylate, 2-ethylhexyl methacrylate, decyl methacrylate, methyl ethacrylate, ethyl ethacrylate, n-butyl ethacrylate, isobutyl ethacrylate, t-butyl ethacrylate, 2-ethylhexyl ethacrylate, decyl ethacrylate, 2,3-dihydroxypropyl acrylate, 2,3-dihydroxypropyl methacrylate, 2-hydroxyethyl acrylate, hydroxypropyl acrylates, 2-hydroxyethyl methacrylate, 2-hydroxyethyl ethacrylate, 2-methoxyethyl acrylate, 2-methoxyethyl methacrylate, 2-methoxyethyl ethacrylate, 2-ethoxyethyl methacrylate, 2-ethoxyethyl ethacrylate, hydroxypropyl methacrylates, glyceryl monoacrylate, glyceryl monomethacrylate, polyalkylene glycol (meth)acrylates, unsaturated sulfonic acids, such as acrylamidopropanesulfonic acid; acrylamide, methacrylamide, ethacrylamide, N-methylacrylamide, N,N-dimethylacrylamide, N-ethylacrylamide, N-isopropylacrylamide, N-butylacrylamide, N-t-butylacrylamide, N-octylacrylamide, N-t-octylacrylamide, N-octadecylacrylamide, N-phenylacrylamide, N-methylmethacrylamide, N-ethylmethacrylamide, N-dodecylmethacrylamide, 1-vinylimidazole, 1-vinyl-2-methylimidazole, N,N-dimethylaminomethyl (meth)acrylate, N,N-diethylaminomethyl (meth)acrylate, N,N-dimethylaminoethyl (meth)acrylate, N,N-diethylaminoethyl (meth)acrylate, N,N-dimethylaminobutyl (meth)acrylate, N,N-diethylaminobutyl (meth)acrylate, N,N-dimethylaminohexyl (meth)acrylate, N,N-dimethylaminooctyl (meth)acrylate, N,N-dimethylaminododecyl (meth)acrylate, N-[3-(dimethylamino)propyl]methacrylamide, N-[3-(dimethylamino)propyl]acrylamide, N-[3-(dimethylamino)butyl]methacrylamide, N-[8-(dimethylamino)octyl]methacrylamide, N-[12-(dimethylamino)dodecyl]methacrylamide, N-[3-(diethylamino)propyl]methacrylamide, N-[3-(diethylamino)propyl]acrylamide; maleic acid, fumaric acid, maleic anhydride and its monoesters, crotonic acid, itaconic acid, diallyldimethylammonium chloride, vinyl ethers (e.g. methyl, ethyl, butyl or dodecyl vinyl ethers), vinylformamide, vinylmethylacetamide, vinylamine; methyl vinyl ketone, maleimide, vinylpyridine, vinylimidazole, vinylfuran, styrene, styrenesulfonate, allyl alcohol, and mixtures thereof.

Of these, particular preference is given to acrylic acid, methacrylic acid, maleic acid, fumaric acid, crotonic acid, maleic anhydride and its monoester, methyl acrylate, methyl methacrylate, ethyl acrylate, ethyl methacrylate, n-butyl acrylate, n-butyl methacrylate, t-butyl acrylate, t-butyl methacrylate, isobutyl acrylate, isobutyl methacrylate, 2-ethylhexyl acrylate, N-t-butylacrylamide, N-octylacrylamide, 2-hydroxyethyl acrylate, hydroxypropyl acrylate, 2-hydroxyethyl methacrylate, hydroxypropyl methacrylate, alkylene glycol (meth)acrylates, unsaturated sulfonic acids such as acrylamidopropanesulfonic acid, vinylpyrrolidone, vinylcaprolactam, vinyl ethers (e.g. methyl, ethyl, butyl or dodecyl vinyl ether), vinylformamide, vinylmethylacetamide, vinylamine, 1-vinylimidazole, 1-vinyl-2-methylimidazole, N,N-dimethylaminomethyl methacrylate and N-[3-(dimethylamino)propyl]methacrylamide; 3-methyl-1-vinylimidazolinium chloride, 3-methyl-1-vinylimidazolinium methylsulfate, N,N-dimethylaminoethyl methacrylate, N-[3-(dimethylamino)propyl]methacrylamide quaternized with methyl chloride, methyl sulfate or diethyl sulfate.

Monomers with a basic nitrogen atom can be quaternized in the following way:

Compounds suitable for quaternizing the amines are, for example, alkyl halides having from 1 to 24 carbon atoms in the alkyl group, e.g. methyl chloride, methyl bromide, methyl iodide, ethyl chloride, ethyl bromide, propyl chloride, hexyl chloride, dodecyl chloride, lauryl chloride and benzyl halides, in particular benzyl chloride and benzyl bromide. Other suitable quaternizing agents are dialkyl sulfates, in particular dimethyl sulfate or diethyl sulfate. The quaternization of the basic amines can also be carried out with alkylene oxides such as ethylene oxide or propylene oxide in the presence of acids. Preferred quaternizing agents are methyl chloride, dimethyl sulfate or diethyl sulfate.

The quaternization can be carried out before the polymerization or after the polymerization.

In addition, it is possible to use the reaction products of unsaturated acids, for example acrylic acid or methacrylic acid, with a quaternized epichlorohydrin of the formula (EV) ($R^{18}=C_1$- to $C_{40}$ alkyl)

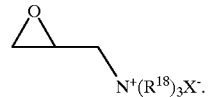

(EV)

Examples thereof are, for example (meth)acryloyloxyhydroxypropyltrimethylammonium chloride and (meth)acryloyloxyhydroxypropyltriethylammonium chloride.

The basic monomers can also be cationized by neutralizing them with mineral acids, such as sulfuric acid, hydrochloric acid, hydrobromic acid, hydroiodic acid, phosphoric acid or nitric acid, or with organic acids, such as formic acid, acetic acid, lactic acid, or citric acid.

In addition to using the abovementioned monomers, the monomers (E) can be macromonomers, such as silicone-containing macromonomers having one or more free-radically polymerizable groups or alkyloxazolene macromonomers, as are described, for exmaple, in EP 408 411.

Furthermore, fluorine-containing monomers, as are described, for example, in EP 558 423, compounds which have a crosslinking action or regulate molecular weight can be used in combination or alone.

The invention likewise relates to the use of polymers which are prepared using monomers of the formula II or contain at least one repeat unit of the formula III, wherein the polymers do not contain groups which have surfactant character associated with an acetoacetoxy function, in cosmetics, in particular in hair cosmetic products, haircare compositions and hair-setting compositions, and to the use of polymers which are prepared using monomers of the formula II or contain at least one repeat unit of the formula III, wherein the polymer is prepared in solution or by bulk polymerization or is used in the dissolved state, in cosmetics, in particular in hair cosmetic products, haircare compositions and hair-setting compositions.

The invention also relates to hair-setting compositions comprising a polymer to which groups of the formula I having the meanings given above are bonded.

The term "hair-setting composition" here includes, preferably, hairspray, setting foam, hair mousse, hair gel, setting lotion and setting cream.

The polymer P can be prepared in the case of the novel use in solution, suspension, emulsion or melt, or be brought into the dissolved, suspended or emulsified state for use.

The polymer P can, in particular, be dissolved, suspended or emulsified in a fluid which comprises at least one of the substances dimethyl ether, propane, butane, ethanol, isopropanol, water and/or halogenated hydrocarbons.

The invention likewise relates to the use of polymers to which groups of the formula I are bonded, and from 95 to 99.95% by weight of which consist of a monomer which does not have the groups of the formula I, in cosmetics, in particular hair cosmetic products.

The invention also relates to copolymers which consist of
a) from 0.05 to 95% by weight of monomers of the formula IIa

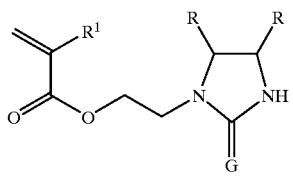

IIa in which $R^1$ is H or $CH_3$,
G is O or NH and
R is H or identical or different organic radicals which may also be bonded to one another, and
b) from 99.95 to 10% by weight of vinylcaprolactam and/or vinylpyrrolidone.

The regulators used for the polymerization of the polymers P can be the customary compounds known to the person skilled in the art, such as sulfur compounds (e.g. mercaptoethanol, 2 ethylhexyl thioglycolate, thioglycolic acid or dodecylmercaptan), and tribromochloromethane and other compounds which have a regulating action on the molecular weight of the resulting polymers.

Where appropriate, it is also possible to use thiol-group-containing silicone compounds.

Preference is given to using silicone-free regulators.

Suitable crosslinking monomers are compounds with at least two ethylenically unsaturated double bonds, such as esters of ethylenically unsaturated carboxylic acids, such as acrylic acid or methacrylic acid and polyhydric alcohols, ethers of at least dihydric alcohols, such as vinyl ethers or allyl ethers. Also suitable are straight-chain or branched, linear or cyclic aliphatic or aromatic hydrocarbons which have at least two double bonds, which in the case of the aliphatic hydrocarbons must not be conjugated. Also suitable are amides of acrylic and methacrylic acid and N allylamines of at least dihydric amines, such as 1,2-diaminoethane, 1,3-diaminopropane. Also suitable are triallylamine or corresponding ammonium salts, N-vinyl compounds of urea derivatives, at least difunctional amides, cyanurates or urethanes. Other suitable crosslinkers are divinyldioxane, tetraallylsilane or tetravinylsilane.

Particularly preferred crosslinkers are, for example, methylenebisacrylamide, triallylamine and triallylammonium salts, divinylimidazole, N,N'-divinylethylene urea, reaction products of polyhydric alcohols with acrylic acid or methacrylic acid, methacrylic esters and acrylic esters of polyalkylene oxides or polyhydric alcohols which have been reacted with ethylene oxide and/or propylene oxide and/or epichlorohydrin.

In the polymerization of the monomers (E) or in the novel use of the polymers P where appropriate, other polymers, such as polyamides, polyurethanes, polyesters, homo- and copolymers of ethylenically unsaturated monomers, may also be present. Examples of such polymers, some of which are also used in cosmetics, are the polymers known under the trade names Amerhold™, Ultrahold™, Ultrahold Strong™, Luviflex™ VBM, Luvimer™, Acronal™, Acudyne™, Stepanhold™, Lovocryl™, Versatyl™, Amphomer™ or Eastman AQ™.

If the monomers (E) contain ionizable groups, they can be neutralized, partially or completely with acids or bases, before or after the polymerization, in order to adjust the solubility or dispersibility in water to a certain level.

Possible neutralizing agents for monomers carrying acid groups are, for example, mineral bases such as sodium carbonate, alkali metal hydroxides and ammonia, organic bases such as aminoalcohols, specifically 2-amino-2-methyl-1-propanol, monoethanolamine, diethanolamine, triethanolamine, triisopropanolamine, tri[(2-hydroxy)-1-propyl]amine, 2-amino-2-methyl-1,3-propanediol, 2-amino-2-hydroxymethyl-1,3-propanediol, and diamines, such as lysine.

Suitable neutralizing agents for monomers carrying cationizable groups are, for example, mineral acids such as hydrochloric acid, sulfuric acid or phosphoric acid, and organic acids such as carboxylic acids, lactic acid, citric acid or others.

It is furthermore possible for auxiliaries, such as plasticizers, film-forming auxiliaries, pigments, perfumes or others, alone or in combination, to be present during the polymerization and/or to be added after the polymerization.

In a preferred embodiment of the invention, no ethylenically unsaturated monomers which have surfactant character associated with an acetoacetoxy function are used for preparing the polymers P (WO 97/45468). This makes it possible to impart to the polymer the interfacial properties which are optimum for the particular intended use once it has been prepared by mixing with suitable surfactants.

In the novel use of the polymers P as hair-setting compositions it is advantageous to set the glass transition temperature of the polymers to values greater than 20° C. by suitable combinations of ethylenically unsaturated monomers.

Particularly preferred ethylenically unsaturated monomers (E) for use in hair-setting polymers are n-butyl acrylate, methyl methacrylate, t-butyl acrylate, ethyl acrylate, styrene, N-t-butylacrylamide, methacrylic acid, acrylic acid, crotonic acid, vinyl acetate, vinyl propionate, vinylcaprolactam, vinylpyrrolidone, vinylimidazole and N-methylvinylimidazolinium salt.

The invention further provides for the use of polymers P in a mixture with other polymers. Particularly suitable polymers in this connection are those customarily used in cosmetics. Such polymers are, for example, poly(meth) acrylates, polyesters, polyurethanes, polymers with quaternized nitrogen atoms, polymers with vinylpyrrolidone, vinylcaprolactam, vinyl acetate or vinyl ether repeat units, polymers with N-alkylated acrylamide repeat units, polymers with 1-(N,N-dimethylamino)-2-ethyl methacrylate repeat units, polymers with imidazolyl radicals (trade names for example Amerhold™, Ultrahold™, Ultrahold Strong™, Luviflex™ VBM, Luvimer™, Acronal™, Acudyne™, Stepanhold™, Lovocryl™, Versatyl™, Amphomer™ or Eastman AQ™).

The invention further provides for the use of polymers which, in addition to said monomers, contain other groups (IX) which, for example, result from the byproducts, specified in DE 4301673 A1, of the synthesis of ureido methacrylate, in particular hydroxyethylethyleneurea (CAS No. 3699-54-5) and N-(methacryloyloxyethyl)-N'-(methacryloyl)ethyleneurea (CAS No. 157312-17-9).

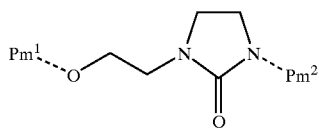

At least one of the two radicals Pm$^1$ and Pm$^2$ is a high molecular weight radical.

EXAMPLES

Examples 1 to 4

50 g of feed 1 and 3.75 g of feed 2 are added dropwise to a stirred initial charge. The mixture is then heated to 78° C. Then, the remainder of feed 1 is added dropwise over the course of 1.5 h, and the remainder of feed 2 is added dropwise over the course of 2 h. The mixture is stirred for a further 2 h. Feed 3 is then added dropwise over the course of 15 min, and the mixture is stirred for a further 2 h at 78° C.

Example 1
Initial charge: 175 g of ethanol
Feed 1: 248 g of t-butyl acrylate, 82.5 g of methacrylic acid, 37.5 g of ethyl acrylate, 15.5 g of a solution of 50% by weight of 2-(2-oxoimidazolidin-1-yl)ethyl methacrylate (CAS number 86261-90-7) in water
Feed 2: 1.5 g of t-butyl perpivalate, 100 g of ethanol
Feed 3: 0.5 g of t-butyl perpivalate, 57.5 g of ethanol

Example 2
Initial charge: 175 g of ethanol
Feed 1: 248 g of t-butyl acrylate, 82.5 g of methacrylic acid, 37.5 g of ethyl acrylate, 75 g of ethanol 36.6 g of a solution of 50% by weight of 2-(2-oxoimidazolidin-1-yl)ethyl methacrylate (CAS number 86261-90-7) in water
Feed 2: 1.5 g of t-butyl perpivalate, 100 g of ethanol
Feed 3: 0.5 g of t-butyl perpivalate, 57.5 g of ethanol

Example 3
Initial charge: 200 g of ethanol
Feed 1: 248 g of t-butyl acrylate, 82.5 g of methacrylic acid, 37.5 g of ethyl acrylate, 18.8 g of a solution of 50% by weight of 2-(2-oxoimidazolidin-1-yl)ethyl methacrylate (CAS number 86261-90-7) in water
Feed 2: 2.5 g of t-butyl perpivalate, 100 g of ethanol
Feed 3: 0.5 g of t-butyl perpivalate, 57.5 g of ethanol

Example 4
Initial charge: 200 g of ethanol
Feed 1: 248 g of t-butyl acrylate, 82.5 g of methacrylic acid, 37.5 g of ethyl acrylate, 75.1 g of a solution of 25% by weight of 2-(2-oxoimidazolidin-1-yl)ethyl methacrylate (CAS number 86261-90-7) in methyl methacrylate
Feed 2: 2.5 g of t-butyl perpivalate, 75 g of ethanol
Feed 3: 0.5 g of t-butyl perpivalate, 57.5 g of ethanol

Example 5

Determination of the pendulum hardness according to König and redispersibility in water The polymers from Examples 1 to 4 and a standard commercial polymer are each dissolved in ethanol and neutralized with 2-amino-2-methyl-1-propanol (AMP) such that the solids content is 20% by weight. The solutions are spread out on a glass plate using a box-type coating bar (slit width 200 μm) to give films and dried for 24 h at room temperature. The pendulum hardness according to König and the redispersibility in water are given in the table.

For comparison purposes, the standard commercial hair-setting polymer Luvimer™ 100 P from BASF Aktiengesellschaft is used. Luvimer 100 P is a copolymer of tert-butyl acrylate, ethyl acrylate and methacrylic acid.

TABLE

| Polymer | Pendulum hardness | Redispersibility |
|---|---|---|
| Example 1 | 162 | complete |
| Example 2 | 153 | complete |
| Example 3 | 148 | complete |
| Example 4 | 155 | complete |
| Luvimer ™ 100 P | 143 | complete |

Example 6

Testing the polymer from Example 1 and a standard commercial polymer (Luvimer™ 100 P from BASF Aktiengesellschaft) for their suitability as hair treatments: the test involves spraying dummy heads with human hair in a half-side test with a defined amount of a standard formulation of the polymers (3 to 4 parts by weight of the polymer, neutralization of the polymer with AMP, 40 parts by weight of dimethyl ether, topped up to 100 parts by weight with ethanol). After drying, the properties of the hair (stickiness, combability, feel, hold, residues, wash-off) are assessed sensorily. It is found that the profile of properties for the polymer from Example 1 is superior to the commercial product Luvimer™ 100 P (FIG. 1).

Example 7

Wash-off is compared as in Example 2, but the polymers are used in VOC-80 formulations (40 parts by weight of the polymer, neutralization of the polymer with 2-aminomethyl-1-propanol, 16 parts by weight of water, 40 parts by weight of dimethyl ether, topped up to 100 parts by weight with ethanol). Wash-off for the polymer from Example 1 is assessed as good (grade "2"), while Luvimer™ 100 P is assessed as satisfactory (grade "3").

Example 8

Solutions of the polymer from Example 1 and of Luvimer™ 100 P, both 45% by weight in ethanol, are investigated using a Haake rheometer. Coaxial cylinders are used as the measuring device. The result shows that the viscosity of the polymer from Example 1 is lower than that of Luvimer™ 100 P (FIG. 2).

We claim:
1. A cosmetic composition adapted for the treatment of hair and comprising, in addition to conventional auxiliaries, at least one (co)polymer which comprises polymer units to which groups of formula I are bonded,

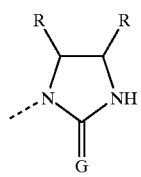

I where
- R is H or identical or different organic radicals, which can also be bonded to one another, and
- G is O or NH, said (co)polymer(s) being present in the composition in an amount which is effective to convey hair-setting properties to the composition.

2. The composition defined in claim 1, wherein the (co)polymer is prepared using monomers of formula II, or the (co)polymer comprises repeating units of formula III,

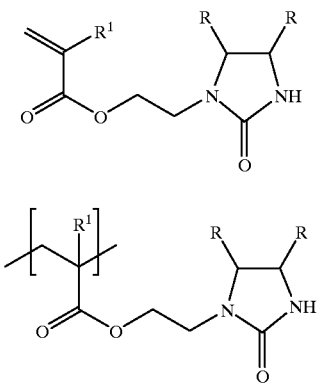

II

III where
- $R^1$ is H or $CH_3$, and
- R is as defined in claim 1.

3. The composition defined in claim 2, wherein the (co)polymer is prepared by polymerization of monomers having olefinic double bonds, and wherein from 0.05 to 100% by weight of the monomers are monomers of formula II, and from 0 to 99.95% by weight are one or more further copolymerizable monomers E.

4. The composition defined in claim 2, wherein the (co)polymer comprises repeating units of formula III and one or more repeating units selected from the group of formulae IV, V, VI, VII and VIII,

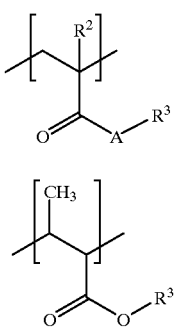

IV

V

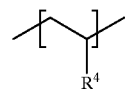

VI

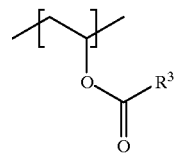

VII

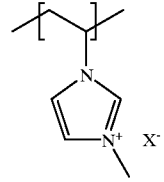

VIII where
- $R^2$ is H or methyl,
- $R^3$ is H or branched or unbranched alkyl radicals which may be substituted by a hydroxyl or amine group,
- $R^4$ is

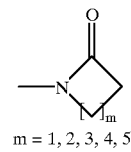

$m = 1, 2, 3, 4, 5$

- A is O or NH,
- X- is an anion, in particular Cl—, $SO_4CH_3$—, $SO_4C_2H_5$—, $H_2PO_4$—.

5. The composition defined in claim 1, wherein the (co)polymer meets at least one of the following conditions: the (co)polymer is prepared in solution, in suspension, in emulsion or in the melt, or the (co)polymer is dissolved, suspended or emulsified for its use in the composition.

6. The composition defined in claim 5, wherein the (co)polymer is dissolved, suspended or emulsified in a fluid which comprises one or more substances selected from the group consisting of dimethyl ether, propane, butane, ethanol, isopropanol, water and halogenated hydrocarbons.

7. The composition defined in claim 1, wherein at least 75% by weight of the (co)polymer consist of monomer units of monomers selected from the group of n-butyl acrylate, methyl methacrylate, t-butyl acrylate, ethyl acrylate, styrene, N-t-butylacrylamide, methacrylic acid, acrylic acid, crotonic acid, vinyl acetate, vinyl propionate, vinylcaprolactam, vinylpyrrolidone, vinylimidazole and N-methylvinylimidazolinium salt.

8. The composition defined in claim 2, wherein the (co)polymer meets at least one of the following conditions: the (co)polymer is prepared in solution or by bulk polymerization, or the (co)polymer is used in the dissolved state.

9. The composition defined in claim 1, which is selected from the group of a hairspray, a setting foam, a hair mousse, a hair gel, a setting lotion or a setting cream.

10. The composition defined in claim 1, wherein from 95 to 99.9% by weight of the (co)polymer consist of monomer units derived from a monomer which does not have groups of formula I.

11. A copolymer consisting of
a) from 0.05 to 90% by weight of monomer units of monomers of formula IIa

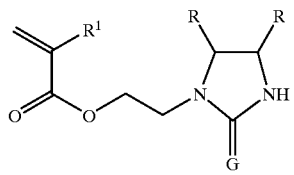

IIa in which
R¹ is H or CH₃,
G is O or NH and
R is H or identical or different organic radicals, which may also be bonded with one another, and
b) from 99.95 to 10% by weight of monomer units of vinylcaprolactam and/or vinylpyrrolidone.

12. A method of improving the hair-setting properties of a cosmetic composition which comprises admixing the composition with an effective amount of at least one (co)polymer which comprises polymer units to which groups of formula I are bonded,

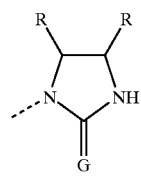

I where
R is H or identical or different organic radicals, which can also be bonded to one another, and
G is O or NH.

13. The method defined in claim 12, wherein the (co)polymers are used in combination with a further polymer.

14. The method of claim 12, wherein the (co)polymer is prepared using monomers of formula II, or the (co)polymer comprises repeating units of formula III,

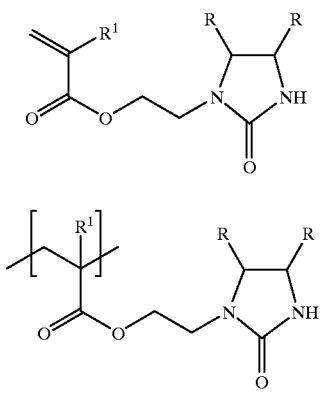

II

III wherein
R¹ is H or CH₃.

15. The method of claim 14, wherein the (co)polymer is prepared by polymerization of monomers having olefinic double bonds, and wherein from 0.05 to 100% by weight of the monomers are monomers of formula II, and from 0 to 99.95% by weight are one or more further copolymerizable monomers E.

16. The method of claim 14, wherein the (co)polymer comprises repeating units of formula III and one or more repeating units selected from the group of formulae IV, V, VI, VII and VIII,

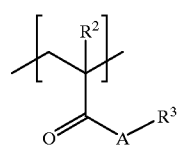

IV

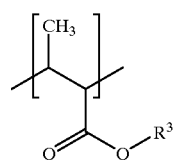

V

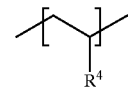

VI

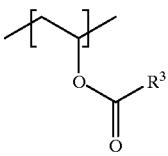

VII

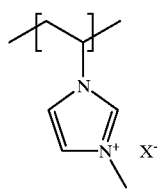

VIII where
R² is H or methyl,
R³ is H or branched or unbranched alkyl radicals which may be substituted by a hydroxyl or amine group,
R⁴ is

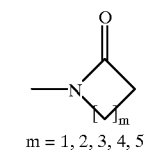

m = 1, 2, 3, 4, 5

A is O or NH,
X− is an anion, in particular Cl—, SO₄CH₃—, SO₄C₂H₅—, H₂PO₄—.

17. The method of claim 14, wherein at least 75% by weight of the (co)polymer consist of monomer units of monomers selected from the group of n-butyl acrylate, methyl methacrylate, t-butyl acrylate, ethyl acrylate, styrene, N-t-butylacrylamide, methacrylic acid, acrylic acid, crotonic acid, vinyl acetate, vinyl propionate, vinylcaprolactam, vinylpyrrolidone, vinylimidazole and N-methylvinylimidazolinium salt.

18. The composition defined in claim 3, wherein the copolymerizable comonomers E are selected from the group of n-butyl acrylate, methyl methacrylate, t-butyl acrylate, ethyl acrylate, styrene, N-t-butylacrylamide, methacrylic acid, acrylic acid, crotonic acid, vinyl acetate, vinyl propionate, vinylcaprolactam, vinylpyrrolidone, vinylimidazole and N-methylvinylimidazolinium salt.

19. The method of claim 15, wherein the copolymerizable comonomers E are selected from the group of n-butyl acrylate, methyl methacrylate, t-butyl acrylate, ethyl acrylate, styrene, N-t-butylacrylamide, methacrylic acid, acrylic acid, crotonic acid, vinyl acetate, vinyl propionate, vinylcaprolactam, vinylpyrrolidone, vinylimidazole and N-methylvinylimidazolinium salt.

* * * * *